United States Patent [19]

Keith et al.

[11] Patent Number: 5,112,967

[45] Date of Patent: May 12, 1992

[54] PROCESS FOR SYNTHESIZING ANTIBACTERIAL CEPHALOSPORIN COMPOUNDS

[75] Inventors: Dennis D. Keith, Montclair; Chung-Chen Wei, Cedar Knolls, both of N.J.; Kevin F. West, Clifton Park, N.Y.

[73] Assignee: Hoffmann-La Roches Inc., Nutley, N.J.

[21] Appl. No.: 515,966

[22] Filed: Apr. 27, 1990

[51] Int. Cl.$^5$ .................. C07D 501/00; C07D 501/14
[52] U.S. Cl. .................................... 540/215; 540/221; 540/230
[58] Field of Search ........................ 540/215, 221, 230

[56] References Cited

U.S. PATENT DOCUMENTS

| | | | |
|---|---|---|---|
| 3,445,463 | 5/1969 | Van Heyningen | 540/222 |
| 3,532,694 | 10/1970 | Somerfield et al. | 540/230 |
| 4,152,432 | 5/1979 | Heymes et al. | 514/207 |

FOREIGN PATENT DOCUMENTS

| | | |
|---|---|---|
| 153874 | 9/1985 | European Pat. Off. |
| 265185 | 4/1988 | European Pat. Off. |

OTHER PUBLICATIONS

J. Med. Chem., 8(1), 22 (1965), Van Heyningen.
J. Med. Chem., 13(6), 1114 (1970) Kokolja.
J. Antibio., 34(10), 1300 (1981) Takaya.
Derwent Abstract of EPA 295 630 (discloses no method of making).

*Primary Examiner*—Robert T. Bond
*Assistant Examiner*—Matthew V. Grumbling
*Attorney, Agent, or Firm*—George M. Gould; George W. Johnston; Alan P. Kass

[57] ABSTRACT

A process for synthesizing 3-acryloxymethyl antibacterialcephalosporin compounds of formula

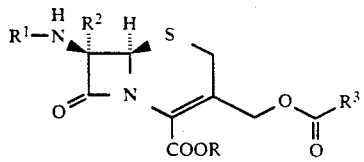

wherein R is hydrogen or a carboxylic acid protecting group; $R^1$ is hydrogen or an acyl group; $R^2$ is hydrogen or lower alkoxy; and $R^3$ is carbocyclic aryl substituted on the ring with one or more members selected from the group consisting of hydroxy, lower alkyl, amino, cyano, lower alkoxy, halogen and alkylcarboxy, as well as the corresponding readily hydrolyzable esters, pharmaceutically acceptable salts and hydrates of these compounds where R is hydrogen, in which a 2-carboxylic acid 3-hydroxymethyl cephalosporin compound is first treated with an organic base to form an organic salt therewith, followed by acylation of the 3-hydroxymethyl substituent.

28 Claims, No Drawings

PROCESS FOR SYNTHESIZING ANTIBACTERIAL CEPHALOSPORIN COMPOUNDS

FIELD OF THE INVENTION

The present invention relates to a process for synthesizing 3-acyloxymethyl $\Delta^3$-cephalosporin compounds, such as antibacterial compounds of the formula

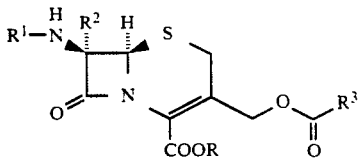

wherein R is hydrogen or a carboxylic group; $R^1$ is hydrogen or an acyl group; $R^2$ is hydrogen or, lower alkoxy, lower alkanoylamino; and $R^3$ is carbocyclic aryl substituted on the ring with one or more members selected from the group consisting of hydroxy, lower alkyl, amino, cyano, lower alkoxy, halogen and alkylcarboxy;
as well as the corresponding readily hydrolyzable esters, pharmaceutically acceptable salts and hydrates of these compounds where R is hydrogen.

BACKGROUND OF THE INVENTION

In the known processes for synthesizing antibacterial cephalosporin compounds, naturally produced cephalosporin C, or a derivative thereof, such as 7-aminocephalosporanic acid (7-ACA), is often used as the starting material. These well-known starting materials can be characterized as having an acetyloxymethyl substituent in the 3-position of the molecule.

In order to obtain synthetic cephalosporins having desirable antibacterial Properties, it is often needed to have an appropriate substituent at the 3'-methyl group of cephalosporins. Among them is the substitution of a different acyloxy group. To achieve this, the starting material (e.g., 7-ACA) is deacetylated with aqueous sodium hydroxide or acetylesterase to yield a 3-hydroxymethyl derivative which is then subjected to acylation with a suitable acyl group.

Typically, the acylation is performed by reacting an acid chloride, for example, with the 3-hydroxymethyl substituent in the presence of a base using the Schotten-Baumann technique. Alternatively, an acid anhydride may be substituted for the acid chloride, although the acid chloride is generally preferred. The base may be sodium hYdroxide or pyridine, for example, depending on the solvent employed. The base neutralizes the hydrogen chloride that would otherwise be liberated, and may also help to catalyze the reaction.

In the above described technique, unwanted side reactions may occur which have the effect of decreasing yields and/or complicating the synthesis. One such unwanted side reaction is the so-called $\Delta^3$ to $\Delta^2$ bond migration (which generally inactivates or at least reduces the antibacterial activity of the resulting cephalosporin compound). An example of a 3-acetyloxymethyl $\Delta^2$-cephalosporin compound would be a compound of the formula

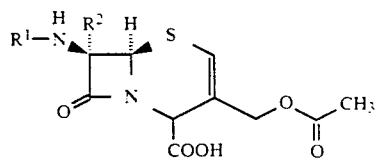

Another unwanted side reaction is known as lactonization—in which the 2-carboxylic acid group of the cephalosporin molecule reacts with the 3-hydroxymethyl substituent to form a lactone. Yet another problem which is encountered in the known synthesis techniques is that a large excess of the acid chloride or of the acid anhydride is often required, particularly when the reaction is carried out in an aqueous medium.

The above-noted problems have long been known in the art. However, little progress has heretofore been made towards a satisfactory solution thereto.

For example, Van Heynigen, J. Med. Chem., Vol. 8, pp 22–25 (1965) describes the preparation of 3-acyloxymethyl derivatives from naturally produced cephalosporin C. First the acetyl group of cephalosporin C is removed by enzymatic hydrolysis using citrus acetylesterase (the orange peel enzyme). The resulting 3-hydroxymethyl derivative is then acylated with either aroyl halides or aliphatic acid chlorides using the Schotten-Baumann technique employing sodium hydroxide in aqueous acetone. The pH of the reaction mixture had to be kept high to get the best yield (to avoid lactone formation). However, the aliphatic acid chlorides reacted preferentially with water and no acylation took Place. Even with the aroYl halides it was found that a large excess of this reagent was necessary to obtain even moderate yields.

Kukolja, S., J. Med. Chem., Vol. 13, pp 1114–1117 (1970), describes a Process using a 3-hydroxymethyl $\Delta^2$-cephalosporin as the starting material (which is reportedly less Prone to lactonization than the corresponding $\Delta^3$ compound). It is acylated using aliphatic acid anhydride in pyridine. The resulting 3-acyloxymethyl $\Delta^2$-cephalosporin is then subjected to an oxidative-reductive process to isomerize the $\Delta^2$- double bond into the $\Delta^3$ position.

To reduce the lactonization side reaction, the following examples describe known acylation procedures which involve the use of the ester of cephalosporanic acids. In each case, the protecting group of the acid eventually has to be removed to yield the biologically active form.

T. Takaya, et. al., The J. of Antiobiotics, Vol. 34, pp.1300–1310 (1981) describes the acylation of the 3-hydroxymethyl function of the ester of cephemoic acids with aliphatic acid chlorides or aroyl chlorides in the presence of triethylamine. A mixture of $\Delta^2$- and $\Delta^3$-acyloxymethylcephems were obtained in these reactions. The desired $\Delta^3$-isomers were prepared from the above mixture by utilizing the oxidative-reductive process for isomerization of the double bond.

U.S. Pat. No. 3,532,694 describes techniques for converting the 3-hydroxymethyl group of cephemoic acids to a 3-acyloxy grouP. As described therein, the carboxylic acid group of the cephemoic acid is first protected with an aralkyl group, e.g. benzyl. The acylation of the 3-hydroxymethyl group is then performed using acid chloride, acid anhydride or mixed acid anhydrides in the presence of an organic base, e.g. pyridine, in an inert anhydrous solvent. It is noted therein that acid chlorides are preferred because the anhydrides tend to give lower yields due to lactone formation. It is also noted therein that $\Delta^3$ to $\Delta^2$ bond migration is a problem encountered with the described techniques, necessitating that the acylation reaction be effected as rapidly as possible.

EP 265,185 describes similar methods for acylating the 3-hydroxymethyl group in $\Delta^3$-cephalosporin compounds by reacting same with an acid halide. The reaction is carried out in a nonaqueous medium, preferably in a chlorinated hydrocarbon solvent such as dichloromethane. Particular examples, wherein pyridine is employed as the base are also disclosed. Although EP 265,185 does not discuss the problems noted above, it appears from the synthesis examples which are described therein that the same problem of low yield was encountered.

Thus, in summary, the known acylation methods have a number of disadvantages, including the following:

(1) $\Delta^3$ to $\Delta^2$ bond migration necessitates further processing of the acyloxymethyl cephalosporin compounds using the oxidative-reductive process to restore the $\Delta^3$ bond;

(2) lactonization reduces yields;

(3) the need to carefully control reaction conditions to reduce $\Delta^3$ to $\Delta^2$ bond migration and lactonization makes the known acylation methods difficult to perform; and (4) a large excess of the acid halide or acid anhydride is generally required.

SUMMARY OF THE INVENTION

The invention provides a novel process for acylating the 3-hydroxymethyl substituent in a $\Delta^3$-cephalosporin compound using an acid halide or acid anhydride in a non-aqueous organic solvent. In accordance with the invention, a 3-hydroxymethyl $\Delta^3$-cephalosporin compound is used as a starting material. A carboxylic acid moiety in the 2-position of this cephalosporin compound is first reacted with an organic base (e.g. a tertiary amine or a quaternary ammonium hydroxide, which is capable of forming an ionic bond with the $-COO^-$ group prior to acylation). The 3-hydroxymethyl group of the resulting compound is then acylated using an acid halide or acid anhydride which is selected to provide the desired acyl group in the 3-position of the cephalosporin molecule, the acylation being carried out in a non-aqueous organic solvent.

It has been found by the inventors that, in contrast to the known acylation techniques wherein the 2-carboxylic acid group is protected e.g., by converting same into an ester, treating the 2-carboxylic acid group with an organic base as described above prior to acylation of the 3-hydroxymethyl substituent affords better yields than were heretofore obtainable and minimize the unwanted side reactions in the heretofore mentioned techniques. Moreover, it has been found by the inventors that, in contrast to the known acylation techniques wherein aqueous sodium hydroxide is used, high yields can be obtained employing the acylation methods in accordance with the invention without using a large excess of the acid halide. In fact satisfactory yields can be achieved using stoichiometric or near-stoichiometric amounts of the acid halide.

Preferred $\Delta^3$-cephalosporin compounds which can be synthesized according to the process of the invention are the compounds of the formula

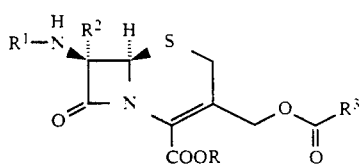

wherein R is hydrogen or a carboxylic acid protecting group; $R^{b1}$ is hydrogen or an acyl group; $R^2$ is hydrogen or lower alkoxy; and $R^3$ is carbocyclic aryl substituted on the ring with one or more members selected from the group consisting of hydroxy, lower alkyl, amino, cyano, lower alkoxy, halogen and alkylcarboxy.

In the process according to the invention the salt of the 3-hydroxymethyl $\Delta^3$-cephalosporin compound, which is formed by treatment with the organic base, need not be isolated prior to acylation. In addition, the subsequent acylation reaction of the 3-hydroxymethyl $\Delta^3$-cephalosporin compound can be carried out in the presence of the organic base. It is also important that the acylation reaction be carried out in a non-aqueous organic solvent, methylene chloride being presently preferred.

Following acylation of the 3-hydroxymethyl substituent, the organic base can be neutralized using conventional techniques, e.g. by treatment with hydrochloric acid.

The free acid form of the $\Delta^3$-cephalosporin compound thus obtained may be subjected to further conventional processing e.g., conversion into pharmaceutically acceptable salts or hydrates as well as readily hydrolyzable esters.

In addition, any substitutions which may be desired in the 7-position of the $\Delta^3$-cephalosporin compound ultimately obtained, may be prepared using conventional techniques, either prior to or after acylation of the 3-hydroxymethyl $\Delta^3$-cephalosporin compound. In the case where the desired substitutions are made at the 7-position prior to acylation of the 3-hydroxymethyl group, the substituents at the 7-position which are susceptible toward acylation conditions may be protected with appropriate protecting groups prior to acylation, the selection of such protecting groups being within the ability of those who are skilled in the art.

DETAILED DESCRIPTION OF THE INVENTION

As used herein, and unless otherwise specified the terms "lower alkyl" and "alkyl" refer to both straight and branched chain saturated hydrocarbon groups having 1 to 8, and preferably 1 to 4, carbon atoms, for example, methyl, ethyl, propyl, isopropyl, tertiary butyl, and the like.

As used herein, and unless otherwise specified the term "lower alkoxy" refers to a straight or branched chain hydrocarbonoxy group wherein the "alkyl" portion is a lower alkyl group as defined above. Examples include methoxy, ethoxy, propoxy and the like.

As used herein, the term "alkylcarboxy" refers to a group having the formula $-COOR_{50}$ wherein $R_{50}$ is alkyl as defined above.

The terms "halogen", or "halo", used herein mean chloro, bromo, iodo and fluoro, unless specified otherwise.

The term "acyl" used herein refers to all organic radicals derived from an organic acid, such as a carboxylic acid, by removal of the hydroxyl group.

Although the group $R^1$ of the formula I compound may be any one of many acyl radicals, certain acyl groups are preferred, as described below.

Exemplary acyl groups are those groups which have been used in the past to acylate Beta lactam antibiotics, including 6-aminopenicillanic acid and derivatives and 7-aminocephalosporanic acid and derivatives; see, for example, *Cephalosporins and Penicillins*, edited by Flynn, Academic Press (1972), Belgian patent 866,083, published October 17, 1978, Belgian patent 867,994, published Dec. 11, 1978, U.S. Pat. No. 4,152,432, issued May 1, 1979, U.S. Pat. No. 3,971,778, issued Jul. 27, 1976, and U.S. Pat. No. 4,173,199, issued Oct. 23, 1979. The portions of these references describing various acyl groups are incorporated herein by reference. The following list of acyl groups is presented to further exemplify the term "acyl", without intending to limit that term to only those groups set forth:

(a) Aliphatic groups having the formula $$R_5-\overset{O}{\underset{\|}{C}}-$$

wherein $R^5$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

[structure]

[structure]

[structure]

[structure]

[structure]

-continued

[structure]

and

[structure]

wherein n is 0, 1, 2 or 3; $R_6$, $R_7$, and $R_8$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_{90}$ is amino, acylamino, hydroxyl, a carboxyl salt, protected carboxy such as benzyloxycarbonyl, formyloxy or azido.

Preferred carbocyclic aromatic acyl groups include those having the formula

[structures]

and

[structure]

($R_{90}$ is preferably an amino group, a hydroxy group, or a carboxyl salt of sulfo salt).

Examples of other acyl groups suitable for the purposes of the present invention are sulfonphenylacetyl, hydroxysulfonloxyphenylacetyl, sulfamoylphenylacetyl, (phenoxycarbonyl)phenylacetyl, (p-tolyloxycarbonyl)phenylacetyl, formyloxyphenylacetyl, carboxyphenylacetyl, formylaminophenylacetyl, benzyloxycarbonylphenylacetyl, 2-(N,N-dimethylsulfamoyl)-2-phenylacetyl, 2-bromo-2-thienylaceyl, etc.

(c) Heteroaromatic groups having the formula

[structures]

wherein n is 0, 1, 2, or 3; $R_{90}$ is as defined above; and $R^{101}$ is a substituted or unsubstituted 5-, 6- or 7-membered heterocyclic ring containing 1, 2, 3 or 4 (preferably 1 or 2) nitrogen, oxygen or sulfur atoms. Exemplary heterocyclic rings are thienyl,furyl, pyrrolyl, pyridinyl, pyrazinyl, thiazolyl, pyrimidinyl and tetrazolyl. Exemplary substituents are halogen, hydroxyl, nitro, amino, cyano, trifluoromethyl, alkyl of 1 to 4 carbon atoms, or alkoxy of 1 to 4 carbon atoms.

Preferred heteroaromatic acyl groups include those groups of the above formulas wherein $R_{101}$ is 2-amino-4-thiazolyl, 2-amino-5-halo-4-thiazolyl, 4-aminopyridin-2-yl, 2-amino-1,3,4-thiadiazol-5-yl, 2-thienyl, 2-furanyl, 4-pyridinyl or 2,6-dichloro-4-pyridinyl.

(d) [[(4-Substituted-2,3-dioxo-1piperazinyl)carbonyl]amino] substituted acetyl groups having the formula

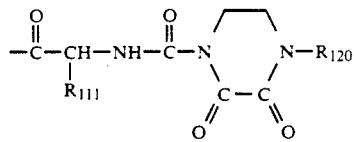

where $R_{111}$ is alkyl, hyroxyalkyl or an aromatic group (including carbocyclic aromatics) such as those of the formula

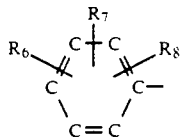

wherein $R_6$, $R_7$ and $R_8$ are as previously defined and heteroaromatics as included within the definition of $R_{101}$; and $R_{120}$ is alkyl, substituted alkyl (wherein the alkyl group is substituted with one or more halogen, cyano, nitro, amino or mercapto groups), e.g. 4-lower alkyl (preferably ethyl or methyl)-2,3-dioxo-1-piperazinecarbonyl-D-phenylglycyl.

(e) (Substituted oxyimino) arylacetyl groups having the formula

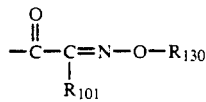

wherein $R_{101}$ is as defined above and $R_{130}$ is hydrogen, lower alkyl and $C_3$-$C_7$ cycloalkyl or substituted lower alkyl wherein the alkyl group is substituted with 1 or more halogen, cyano, nitro, amino, mercapto, lower alkylthio, aromatic group (as defined by $R_{111}$), carboxyl(including salts thereof), amido, carbamoyl, lower alkoxycarbonyl, phenylmethoxycarbonyl, diphenylmethoxycarbonyl, carboxyl lower alkyl or carboxyl-$C_3$-$C_7$-cycloalkyl. Examples of the

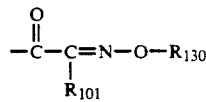

grouping are 2-[(2-chloroacetamidothiazol-4-yl)-2-(p-nitro)-benzyloxycarbonyl]methoxyimino]acetyl, 2-(2-chloroacetamidothiazol-4-yl)-2-methoxyiminoacetyl, 2-(2-aminothiazol-4-yl)-2-isopropoxyiminoacetyl), 2-(2-aminothiazol-4-yl)-2-methoxyiminoacetyl, 2-(2-amino-thiazol-4-yl)-2-hydroxyiminoacetyl, 2-thienyl-2-methoxyiminoacetyl, 2-furyl-2-methoxyiminoacetyl, 2-(4-hydroxyphenyl)-2-methoxyiminoacetyl, 2-phenyl-2-methoxyiminoacetyl, 2-phenyl-2-hydroxyiminoacetyl, 2-thienyl-2-hydroxyiminoacetyl, 2-thienyl-2-(dichloroacetyloxyimino)acetyl, 2-[4-(gamma-D-glutamyloxy)phenyl]-2-hydroxyiminoacetyl, 2-(5-chloro-2-chloroacetamidothiazol-4-yl)-2-methoxyiminoacetyl, 2-(5-chloro-2-aminothiazol-4-yl)-2-methoxyiminoacetyl, 2-[2-(t-butoxycarbonyl)isopropoxyimino]-2-(2-sulfoaminothiazol-4-yl)acetyl, 2-[2-(t-butoxycarbonyl)isopropoxyimino]-2-(2-triphenylmethylaminothiazol-4-yl)acetyl, 2-(2-chloroacetamidothiazol-4-yl)-2-(isopropoxyimino)acetyl, 2-methoxyimino-2-(2-sulfoaminothiazol-4-yl)acetyl, 2-[(2-aminothiazol-4-yl)-2-carboxymethoxyimino]acetyl, 2-[(2-mesylaminothiazol)-4-yl]-2-isopropoxyiminoacetyl, 2-(2-imino-3-mesYl-4-thiazolin-4-yl)-2-isopropoxyiminoacetyl, 2-(2-aminothiazol-4-yl)-2-(carboxyisopropoxyimino)acetyl, etc.

(f) (Acylamino) substituted acetYl groups having the formula

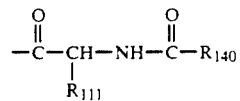

wherein $R_{111}$ is as defined above and $R_{140}$ is

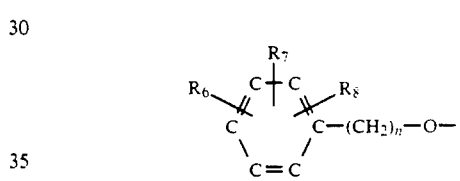

(where $R_6$, $R_7$, $R_8$ and n are as previously defined), hydrogen, lower alkyl, substituted lower alkyl, amino, alkylamino, dialkylamino, (cyanoalkyl)amino, hydrazino, alkyl hydrazino, aryl hydrazino and acyl hydrazino.

Preferred (acylamino)arylacetyl groups of the above formula include those groups wherein $R_{140}$ is amino, or acylamino. Also Preferred are those groups wherein $R_{111}$ is phenyl or 2-thienyl.

(g) (Substituted acylalkoxyimino) substituted acetyl groups having the formula

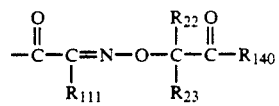

wherein $R_{111}$ and $R_{140}$ are as defined above, and $R_{22}$ and $R_{23}$ are independently selected from the group consisting of hydrogen and lower alkyl, or $R_{22}$ and $R_{23}$ taken together with the carbon atom to which they are attached form a $C_3$-$C_7$ carbocyclic ring, for example, cyclopropyl, cyclobutyl or cyclopentyl.

Preferred (substituted acyloxyimino) arylacetyl groups of the above formula include those groups wherein $R_{140}$ is amino. Also preferred are those groups wherein $R_{111}$ is 4-(2-amino-thiazolyl).

(h) [[[3-Substituted-2-oxo-1-imidazolidinyl]Carbonyl]amino] substituted acetyl groups having the formula

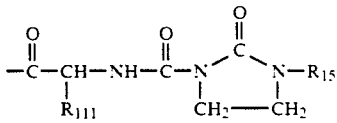

wherein $R_{111}$ is as defined above and $R_{15}$ is hydrogen, alkylsulfonyl, arylmethyleneamino (i.e., $-N=CHR_{111}$ wherein $R_{111}$ is as defined above),

(wherein $R_{16}$ is hydrogen, alkyl or halogen substituted alkyl), aromatic group (as defined by $R_{111}$ above), alkyl or substituted alkyl (wherein the alkyl group is substituted with one or more halogen, cyano, nitro, amino or mercapto groups).

Preferred [[[3-substituted-2-oxo-1-imidazolidinyl]carbonyl]amino] substituted acetly groups of the above formula include those wherein R111 is phenyl or 2-thienyl. Also preferred are those groups wherein $R_{15}$ is hydrogen, methylsulfonyl, Phenylmethylenamino or 2-furylmethylenamino.

By the terms "aryl" and "carbocyclic aryl" are meant an aromatic moiety, such as, phenyl. tolyl, xylyl, mesityl, cumenyl, naphthyl, and the like, which may be unsubstituted or substituted with 1 to 3 suitable substituents, such as halo (fluoro, chloro, bromo, etc.), hydroxy, lower alkyl, amino, cyano, lower alkoxy, alkylcarboxy, and the like.

By the term "lower alkanoyl" or "alkanoyl" as utilized herein is intended a moiety of the formula

wherein $R_{25}$ is H or $C_1$ to $C_6$ lower alkanoic acid, e.g., acetyl, formyl, propionyl, butyryl and the like.

By the term "substituted phenyl" is meant phenyl mono-or di-substituted by halo(chloro, bromo, fluoro, etc.), lower alkyl, amino, nitro or trifluoromethyl.

By the term "substituted alkyl" is meant a "lower alkyl" moiety substituted by, for example, halo (chloro, fluoro, bromo, etc.), trifluoromethyl, amino, cyano, etc.

By the terms "alkenyl" and "lower alkenyl" are meant straight or branched chain hydrocarbon groups which contain an olefinic double bond having 2 to 6 carbon atoms, i.e. the radical of compounds of the formula $C_nH_{2n}$ wherein n is 2 to 6, e.g. propenyl, vinyl, etc.

By the term "aralkyl" is meant a hydrocarbon group having both aromatic and aliphatic structures, that is, a hydrocarbon group in which a lower alkyl hydrogen atom is substituted by a monocylic aryl group, e.g., phenyl, tolyl, etc.

The expression "5- or 6- membered heterocyclic rinq containing 1-3 hetero atoms selected from the group consisting of O, N and S" is intended to represent the following groups: pyridyl, piperidyl, piperidino, N-oxido-pyridyl, pyrimidyl, piperazinyl, pyrolidinyl, pyridazinyl, N-oxide-pyridazinyl, etc. a 5-membered nitrogen-containing hetero ring, e.g. pyrazolyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tet- razolyl, etc., and others. Each of these hetero rings may be further substituted and, as the substituents, there may be mentioned, for example, lower alkyls such as methyl, ethyl, propyl, etc., lower alkoxys such as methoxy, ethoxy, etc., halogens such as chlorine, bromine, etc., halogen substituted alkyls such as trifluoromethyl, trichloroethyl, etc., amino, mercapto, hydroxyl, carbamoyl, carboxyl group, etc.

By the term "cycloalkenyl" is meant a 3-6 membered unsaturated carbocyclic moiety, e.g. cyclobutenyl, cyclohexenyl, etc.

By the term "$\Delta^3$-cephalosporin" is meant a compound of the formula

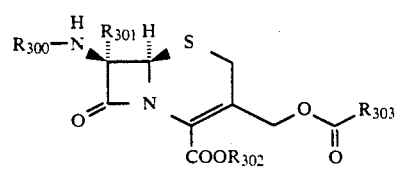

wherein $R_{300}$ is any moiety which may be employed in the antibacterial art as a substituent on the amino group in the 7-position, $R_{301}$ is any moiety which may be employed in the antibacterial art as a substituent in the 7-position $R_{302}$ is any moiety which may be employed in the antibacterial art as a substituent on the carboxylic acid group in the 2-position, and $R_{303}$ is any moiety which may be employed in the antibacterial art for forming an acyloxymethyl substituent in the 3-position. Preferably, $R_{303}$ is phenyl or naphthyl which may be optionally mono-, di- or tri-substituted with $C_1$-$C_6$ lower alkyl (preferably $C_1$-$C_3$ lower alkyl), $C_1$-$C_6$ lower alkoxy (preferably $C_1$-$C_3$ lower alkoxy), hydroxy, amino, cyano, halogen or alkylcarboxy.

By the term "3-hydroxymethyl $\Delta^3$-cephalosporin" is meant a compound of the formula:

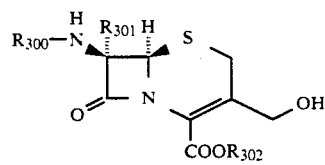

wherein $R_{300}$, $R_{301}$ and $R_{302}$ are the same as above.

As readily hydrolyzable esters of the compounds of formulas I and Ia there are to be understood compounds of formulas I and Ia, the carboxy group(s) of which (i.e., the 2-carboxy group) is/are present in the form of readily hydrolyzable ester groups. Examples of such esters, which can be of the conventional type, are the lower alkanoyloxyalkyl esters (e.g., the acetoxymethyl, pivaloyloxymethyl, 1-acetoxyethyl and 1-pivaloyloxyethyl ester), the lower alkoxycarbonyloxyalkyl esters (e.g. the methoxycarbonyloxymethyl, 1-ethoxycarbonyloxyethyl and 1-isopropoxycarbonyloxyethyl ester), the lactonyl esters (e.g., the phthalidyl and thiophthalidyl ester), the lower alkoxymethyl esters (e.g. the methoxymethyl ester) and the lower alkanoylaminomethyl esters (e.g., the acetamidomethyl ester). Other esters (e.g. the benzyl and cyanomethyl esters) can also be used.

It is to be understood that in accordance with the invention, when acylating a 3-hydroxymethyl $\Delta^3$-cephalosporin compound, the 2-carboxylic acid moiety is not protected, for example, with conventional protecting groups such as esters. Rather, prior to acylation, the carboxylic acid group in the 2-position of the 3-hydroxymethyl Δ³-cephalosporin compound to be acylated is treated with an organic base (preferably, a tertiary or quaternary ammonium hydroxide—most preferably, triethylamine) which is capable of forming an ionic bond therewith. Additionally, as inorganic salts generally are not soluble in nonaqueous organic solvents, such inorganic salts are not preferred for use in the acylation step according to the invention.

Following the acylation step, the orqanic base employed may be removed by conventional methods as will be described below. If desired the obtained product may then be converted into any of a number of pharmaceutically acceptable salts. Examples of such pharmaceutically acceptable salts of the compounds of formulas I and Ia are alkali metal salts such as the sodium and potassium salt, the ammonium salt, alkaline earth metal salts such as the calcium salt, salts with organic bases such as salts with amines (e.g., salts with N-ethyl-piperidine, procaine, dibenzylamine, N,N'-dibenzylethylenediamine, alkylamines or dialkylamines) as well as salts with amino acids such as, for example, salts with arginine or lysine.

The compounds of formulas I and Ia as well as their salts and readily hydrolyzable esters can be hydrates. The hydration can be effected in the course of the manufacturing process or can occur gradually as a result Of hygroscopic properties of an initially anhydrous product.

A Preferred class of compounds which can be made using the processes according to the invention are of the formula

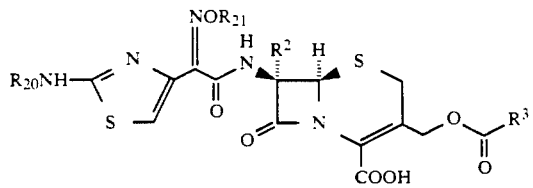

wherein $R^2$ and $R^3$ are as above, $R_{20}$ is hydrogen or an amino protecting group, for example, trityl or chloroacetyl, and $R_{21}$ is hydrogen, lower alkyl or a group of the formula

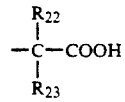

wherein $R_{22}$ and $R_{23}$ are as defined above.

A still more preferred class of compounds which can be made using the processes according to the invention are of the formula II in which $R_{20}$ is hydrogen, and $R_{21}$ is methyl or a group of the formula

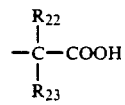

wherein $R_{22}$ and $R_{23}$ are hydrogen or methyl.
Preferably, the

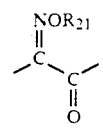

group is in the syn- form, i.e., the Z-form.

Another preferred class of compounds which can be made using the processes according to the invention are of the formula

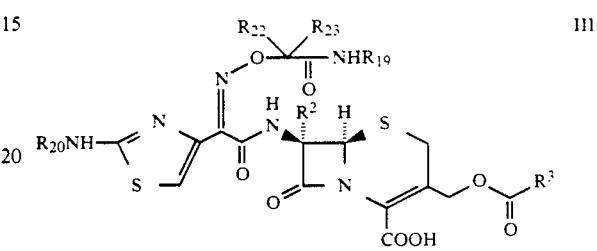

wherein $R^2$ and $R^3$ are as above, $R_{19}$ is hydrogen, lower alkyl, aminoalkyl, amino, arylamino or acylamino, and $R_{20}$, $R_{22}$ and $R_{23}$ are as defined above.

Still another preferred class of compounds which can be made using the processes according to the invention are those of the formula

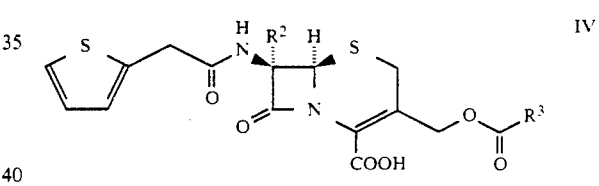

wherein $R^2$ and $R^3$ are as above.

Other preferred compounds which can be made using the processes according to the invention are of the formula

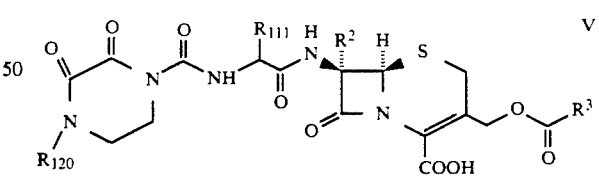

wherein $R^2$, $R^3$, $R_{111}$ and $R_{120}$ are defined as above.

$R^3$ is preferably of the formula

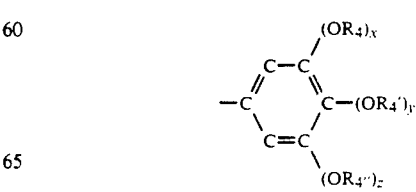

or of the formula

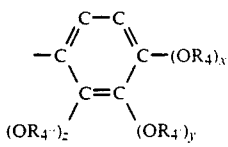

or of the formula

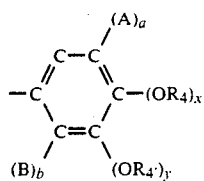

wherein $R_4$ $R_4$, and $R_{4''}$ are independently hydrogen or

wherein $R_{200}$ is straight or branched lower alkyl, A and B are halogen, and a, b, x, y and z are independently zero or 1 except that at least two of x, y and z are always 1. When a, b, x, y or z is zero, it should be understood that a hydrogen atom will then be present at that ring position.

Compounds of the formula I and Ia, including their active geometric and/or optical isomers, their salts and esters and hydrates of those compounds can be used as agents to combat bacterial infections (including urinary tract infections and respiratory infections) in mammalian species, e.g., dogs, cats, horses, etc., and humans. These compounds and Gram-positive bacteria. The in vivo activity of selected compounds of formulas I and Ia as measured by the Minimum Inhibitory Concentration in micrograms/ml utilizing the Agar Well Diffusion Method, Agar Dilution Method or Broth Dilution Method against a variety of Gram-positive and Gram-negative organisms, is as follows:

| | |
|---|---|
| Compound A: | [6R-[6 alpha,7 beta(Z)]]-7-[[2-amino-4-thiazolyl)(methoxyimino)acetyl]amino]-3-[[[(3,4-dihydroxyphenyl)carbonyl]oxy]methyl]-8-oxo-5-thia-1-azabicyclo[4.2.0]oct-2-ene-2-carboxylic acid monosodium salt |
| Compound B: | [6R-[alpha,7 beta(Z)]]-3-[[[3,4-bis(acetyloxy)benzoyl]oxy]methyl]-7-[[[2-amino-4-thiazolyl][(2-amino-2-oxoethoxy)imino]acetyl]amino]-8-oxo-5-thia-1-azabicyclo[4.2.0]oct-2-ene-2-carboxylic acid monosodium salt |
| Compound C: | [6R-[6 alpha,7 beta(Z)]]-7-[[(2-amino-4-thiazolyl)(1-carboxy-1-methylethoxy)imino]acetyl]amino]-3-[[(3,4-dihydroxybenzoyl)oxy]methyl]-8-oxo-5-thia-1-azabicyclo[4.2.0]oct-2-ene-2-carboxylicacid disodium salt |
| Compound D: | [6R-[6 alpha,7 beta(R*)]]-7-[[[[(4-ethyl-2,4-dioxo-1-piperazinyl)carbonyl]amino]phenylacetyl]amino-3-[[(3,4-dihydroxy)benzoyl]oxy]methyl]-8-oxo-5-thia-1-azabicyclo[4.2.0.]-oct-2-ene-2-carboxylic acid monosodium salt |

TABLE 1

| In Vitro (MIC (mg/ml) Agar Well Diffusion Method | |
|---|---|
| Culture | Compound A |
| P. aeruginosa 56 | 0.98 |

TABLE 1-continued

| In Vitro (MIC (mg/ml) Agar Well Diffusion Method | |
|---|---|
| Culture | Compound A |
| P. vulgaris 101N | 0.06 |
| E. coli 1269B | 0.12 |
| K. pneumonia 369 | 0.49 |
| S. marcescens SM | 0.98 |
| S. aureus 1059B | 7.8 |

TABLE 2

| In Vitro MIC (ug/ml) Agar Dilution Method | |
|---|---|
| Culture | Compound B |
| E. coli 48 | 0.031 |
| K. pneumoniae A | 0.125 |
| E. cloacae 9570A | 1 |
| E. cloacae P99 | 32 |
| P. vulgaris ATCC 6380 | 0.016 |
| P. mirabilis 190 | 0.063 |
| S. marscescens SM | 1 |
| P. aeruginosa 130 | 4 |
| P. aeruginosa 185/H | 2 |
| P. aeruginosa Stone 130 | 4 |
| S. aureus Giorgid | 8 |
| S. aureus Smith | 4 |
| S. aureus 95 | 64 |
| S. aureus 1059B | 4 |
| S. aureus ATCC 25923 | 2 |

TABLE 3

| In Vitro MIC (ug/ml) Broth Dilution Method | | | |
|---|---|---|---|
| | Compounds | | |
| Culture | A | C | D |
| P. aeruginosa B | 2 | 0.125 | 0.25 |
| P. aeruginosa Stone 130 | 2 | 0.125 | 0.5 |
| P. aeruginosa ATCC 27853 | 8 | 32 | 0.5 |
| P. aeruginosa 8710 | 2 | 0.063 | 0.125 |
| P. aeruginosa 503-56 | 4 | 0.25 | 4 |
| P. aeruginosa 8780 | 0.5 | >0.008 | 0.016 |
| P. aeruginosa 6148B | 2 | 0.031 | 0.125 |
| P. aeruginosa 765 | 4 | 8 | 128 |
| P. aeruginosa 185/H | 0.016 | 0.031 | 0.125 |
| P. aeruginosa 1973E | 4 | 2 | 4 |
| P. aeruginosa 5700 | 8 | 2 | 4 |
| P. aeruginosa K77/WT | 1 | 0.63 | 0.25 |
| P. aeruginosa K77/61 | 0.25 | >0.008 | 0.016 |

For combatting bacterial infections in mammals, a compound of formulas I and Ia (more precisely, a compound of formula I where R is hydrogen and $R^1$ is not hydrogen, or a corresponding hydrolyzable ester or pharmaceutically acceptable salt or hydrate) can be administered to a mammal in the amount of about 5 mg/kg/day to about 500 mg/kg/day, preferably about 10 mg/kg/day to 100 mg/kg/day, most preferably about 10 mg/kg/day to about 55 mg/kg/day.

All modes of administration which have been uSed in the Past to deliver penicillins and cephalosporins to the site of the infection are also contemplated for use with the compounds of formulas I and Ia. By way of illustration, such methods of administration include oral (e.g., tablets or capsules), parenteral (e.g., intravenous or intramuscular), and enteral (e.g., as a suppository).

The following reaction schemes set forth the methods and intermediates useful in producing the end products of formulas I and Ia.

In the following reaction sequences, where a substituent group is present which may be susceptible toward the reaction conditions, it should be in protected form, utilizing well known protecting groups. For example, amino groups may be protected with easily removable protecting groups employed in peptide chemistry. such as an alkoxycarbonyl group, e.g., t-butoxycarbonyl, and the like or substituted alkyl, e.g. triphenylmethyl and the like.

As ester protecting groups one may utilize an ester from which can be easily converted into a free carboxyl group under mild conditions, the ester protecting group being exemplified by, for example, t-butyl, p-nitrobenzyl, benzhydryl, allyl, etc.

wherein $R_{400}$, $R_{401}$ and $R_{402}$, which may be the same or different, are $C_1$-$C_3$ alkyl, most preferably triethylamine. Quaternary ammonium hydroxide of the formula

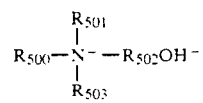

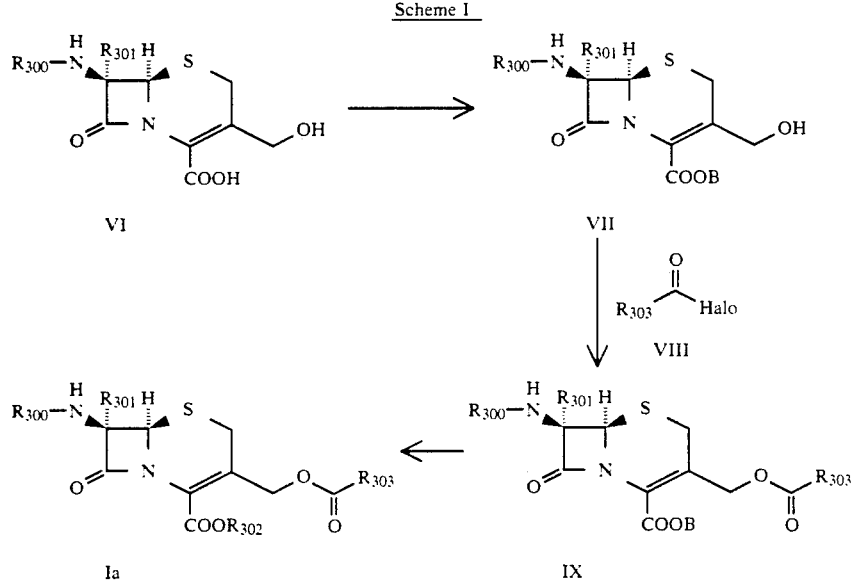

Where $R_{300}$, $R_{301}$, $R_{302}$ and $R_{303}$ are as defined above, B is an organic cation which is capable of forming an ionic bond with the —COO$^-$ group, particularly a protonated tertiary amine or a quaternary ammonium group and Halo is as defined above. In the case of compound VIII, when $R_{303}$ is phenyl or naphthyl substituted with either hydroxy or amino, the hydroxy or amino, as the case may be, should be in protected form. For example, both hydroxy and amino can be protected using an acyl group. Amino can also be protected using a $C_1$-$C_3$ alkoxycarbonyl group, for example.

SCHEME I

VI→VII

The compound of formula VI, which is known or made by analogy (see, e.g. Takaya, et al., J. Antibiotics, Vol. 34, p. 1300–1310 (1981) and U.S. Pat. No. 3,445,463 as well as European Patent Application No. 265,185) is reacted with the organic base in a non-aqueous organic solvent, preferably a non-polar organic solvent, most preferably methylene chloride. Other non-aqueous organic solvents which may be employed include 1,2-dichloroethane, acetonitrile and tetrahydrofuran. The organic base is preferably a tertiary amine of the formula $$R_{400}-\underset{\underset{R_{402}}{|}}{\overset{\overset{R_{401}}{|}}{N}}-R_{402}$$

wherein $R_{500}$, $R_{501}$, $R_{502}$, and $R_{503}$, which may be the same or different are $C_1$-$C_4$ alkyl, may also be employed in accordance with the invention, although tertiary amines are presently preferred. The reaction is preferably run between about 0° C. and room temperature (e.g. 23°–25° C.). The resulting compound of formula VII can be isolated using known isolation techniques, if desired.

VII+VIII→IX

The acid halide of formula VIII is known or made using conventional methods. Preferably the compound of formula VIII is formed in situ from the corresponding carboxylic acid. Fluorine is a preferred halo moiety for the acid halide of formula VIII. The acid halide of formula VIII is reacted with the compound of formula VII, preferably at a temperature of between 0° C. and room temperature and the reaction is carried out in a non-aqueous organic solvent as described above to form compound IX.

IX→Ia

The organic base is removed from compound IX using conventional techniques, preferably by treatment with hydrochloric acid. A compound of the formula Ia wherein $R_{302}$ is hydrogen is thus obtained, which upon further processing if desired, can be converted into a pharmaceutically acceptable salt or a readily hydrolyzable ester as well as a hydrate thereof using conventional techniques.

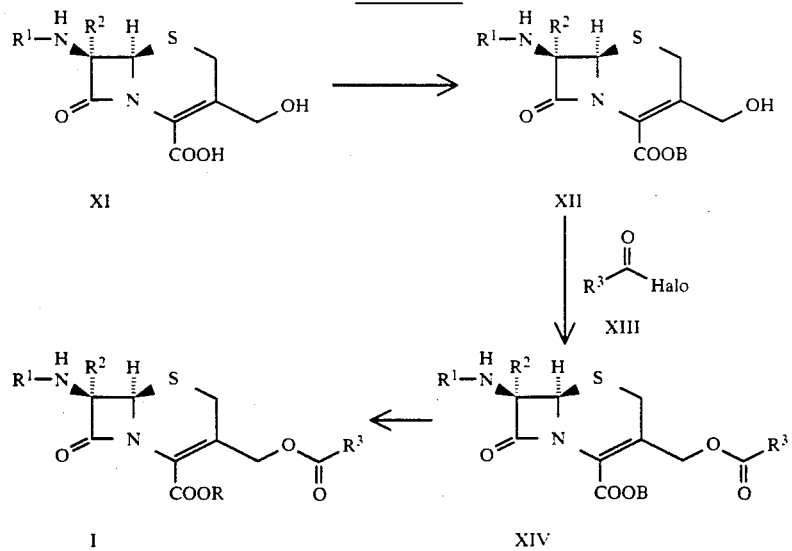

Wherein R, $R^1$, $R^2$, $R^3$ and B are as above defined.

SCHEME II

XI–XII

The compound of formula XI, which is known or made by analogy (see, e.g., Takaya, et al., J. Antibiotics, Vol. 34, pp 1300–1310 (1981) and U.S. Pat. No. 3,445,463 as well as European Patent Application No. 265,185) is reacted with the organic base, as defined above, in a non-aqueous organic solvent, also as defined above. The reaction is preferably run between about 0° C. and room temperature. The resulting compound of formula XII can be isolated using known isolation techniques, if desired.

XII + XIII → XIV

The acid halide of formula XIII is known or made using conventional methods. Preferably the compound of formula XIII is formed in situ from the corresponding carboxylic acid. Fluorine is a preferred halo moiety in the compound of formula XIII. The acid halide of formula XIII is reacted with the compound of formula XII preferably at a temperature between about 0° C. and room temperature and the reaction is carried out in a non-aqueous organic solvent, as described above, to form compound XIV.

XIV → I

The organic base is removed from compound XIV using conventional techniques, preferably by treatment with hydrochloric acid. A compound of formula I wherein group B is replaced by hydrogen is thus obtained, which upon further processing if desired oan be oonverted into a pharmaceutically acceptable salt or readily hydrolyzable ester, as well as a hydrate thereof usinq conventional techniques.

In Scheme II, an amino protecting group $R_{600}$ can be instead of the substituent $R^1$. After acylation of the 3-hydroxymethyl group, the amino protecting group can be replaced with a substituent $R^1$ as defined above.

Additionally, in the reaction schemes described above, the acid halide, i.e. the compound of formula VIII in Scheme I and of formula XIII in Scheme II, can be replaced with a corresponding acid anhydride or an acid carbonate. Thus, compound VIII can be replaced with a compound of formula

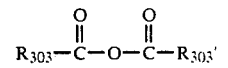

or

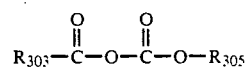

wherein $R_{303}$, has the same definition as $R_{303}$ above and $R_{303}'$ and $R_{303}$ may be the same or different and $R_{305}$ has the same definition as $R_{303}$ and is preferably different from $R_{303}$ Similarly, compound XIII can be replaced by a compound of the formula

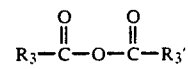

or

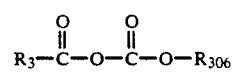

wherein $R_3$ has the same definition as $R_3$ above and $R_3$ and $R_3$ can be the same or different and $R_{306}$ has the same definition as $R_3$ and is preferably different from $R_3$.

In the processes according to the invention, it is preferred, however, to use an acid halide, most preferably an acid fluoride, for acylation of the 3-hydroxymethyl substituent of the cephalosporin compound.

EXAMPLE

Step 1

(6R-trans)-3-[[[3,4-bis(acetyloxy)benzoyl]oxy]methyl]-7-[[1,1-dimethylethoxycarbonylamino1-8-oxo-5-thia-1-azabicyclo[4.2.0]oct-2-ene-2-carboxylic acid To a magnetically stirred 1 liter flask was added 29.75 g of 3,4-diacetoxybenzoic acid in 375 mL of methylene chloride, 52.5 mL of triethylamine followed by the addition of 250 mL of methylene chloride. The solution was cooled to 0° C. in an ice bath, and 29.78 g of N-methyl-2-fluoropyridinium tosylate was added. Stirring was continued at 0° C. for 1 hour followed by the addition of 37.78 g of (6R,7R)-7-[[1,1-dimethylethoxycarbonyl]amino]-3-(hydroxymethyl)-8-oxo-5-thia-1-azabicyclo-(4.2.0)oct-2-ene2-carboxylic acid. After stirring for an additional 20 minutes, the solution was allowed to warm to RT. The reaction mixture was poured into a mixture of 1500 mL of ethyl acetate and 1500 mL of 1.0N hydrochloric acid. The organic phase was separated and to this added 1500 mL of 2% sodium bicarbonate, 50 mL hexane, and 1800 mL brine. A slow separation of the phases occurs and the organic portion was removed and washed with 1500 mL of brine. The organic solution was separated, dried over sodium sulfate and the solvent removed in vacuo to give 47.45 g (76.67%) of the named product.

Step 2

(6R-trans)-3-[[[3,4-bis(acetyloxy)benzoy]oxy]methyl]-7-amino-8-oxo-5-thia-1-azabicyclo[4.2.0]oct-2-ene-2carboxylic acid To a magnetically stirred 500 mL flask under argon at room temperature (about 23° C.) was added 25.69 g of (6R-trans)-3-[[[3,4-bis(acetyloxy)-benzoyl]oxy]methyl-7-[[1,1dimethylethoxycarbonyl]amino]-8-oxo-5-thia-1-azabicyclo[4.2.0]oct-2-ene-2-carboxylic acid and 250 mL of methylene chloride. This was followed by the addition of 25 mL of anisole and 250 mL of trifluoroacetic acid. Stirring was continued for 3 hours and then the solvents removed in vacuo. To the oil residue was added 200 mL of ethyl acetate and stirred for 20 minutes causing precipitation. 650 mL of anhydrous ether was added to this suspension and stirred for 10 minutes. The mixture was filtered on a Buchner funnel and dried under high vacuum to give 20.25 g (76.9%) of the named product.

Step 3

[6R-[6 alpha, 7 beta(Z)]]-7-[[[2-[amino[2-amino-2-oxoethoxy]-imino-4-thiazoly]acetyl]amino1-3-[[[3,4-dihydroxybenzoy]oxy]-methy-8-oxo-5-thia-1-azabicyclo[4,2]oct-2-ene-2-carboxylic acid To a mechanically stirred 1 liter flask was added 20.25 g of (6R-trans)-3-[[[3,4-bis(acetyloxy)benzoyl]oxy]methyl]-7-amino-8-oxo-5-thia-1-azabicyclo[4.2.0]oct-2-ene-2-carboxylic acid in 300 mL of THF giving a tan slurry. 5.88g of sodium bicarbonate in 400 mL of water was added to the above slurry and stirring was continued until solution occurred. To this was added 18.78 g of S-2-mercaptobenzthiazolyl-2-(2-aminothiazol-4-yl)-2-(Z)-formamidomethoxyiminoacetate, which is known or can be made by conventional synthesis techniques. The resulting solution was stirred at room temperature for 5 hours, then Poured into 1600 ml of ethyl acetate and washed with a solution of 3.00 g of sodium bicarbonate in 400 mL of water. Aqueous layer was separated and filtered through celite and the celite was washed with a small amount of water. The filtrate was washed with 1600 mL of ethyl acetate and the aqueous layer again separated and to this was added 77 mL of methanol and 15.85 g of sodium bicarbonate. This solution was stirred for 1 hour at RT, and the organic solvents removed in vacuo. The pH was adjusted to 2.8 with 1.0N HCl (approx. 240 mL) while cooling in an ice bath. The precipitate formed was filtered on a Buchner funnel, and the filter cake covered with a latex membrane and compressed to squeeze out solvent. The cake was then dried in vacuo to give 24.97 g (117%) (water still present) of the named compound.

Step 4

[6R-[6alpha,7beta(Z)]1-7-[[[2-amino-2-amino-2-oxoethoxy]imino-4-thiazolyl]acetyamino]-3-[[3,4-dihydroxybenzoy]oxy]methyl-8-oxo-5-thia-1-azabioyclo[4.2.-0]oct-2-ene-2-carboxylic acid monosodium salt In a 3 liter Erlenmeyer flask was placed 45.3 g of crude [6R-[6alpha,7beta(Z)]]-7-[[[2-amino[2-amino-2[oxoethoxy]imino-4-thiazolyl]acetyl]amino]-3-[[[3,4dihydroxybenzoyl]oxy]methyl]-8-oxo-5-thia-1-azabicyclo[4.2.0]oct-2-ene-2-carboxylic acid and to this was added 800 mL of 10% water in acetone. The mixture was stirred for 25-30 minutes until most of the material dissolved, at which time it was diluted to a volume of 3 liters with acetone. The precipitate was filtered and the filtrate transferred to a 5 liter 3-neck flask equipped with a mechanical stirrer and a dropping funnel containing 8.50 g of sodium 2-ethylhexanoate in 1000 mL of acetone. The precipitate from above was stirred in 50 mL of 1:1 acetone/$H_2O$ for 15 minutes, filtered, and the filtrate added to the above 5 liter flask. The sodium 2-ethylhexanoate was then added dropwise over a period of 2 hours. The mixture was then filtered, compressed with a latex membrane and dried on the Buchner funnel for 20 minutes. The material was dissolved in 150 mL of water, cooled in the refrigerator 3 hours and filtered. The cake was washed with a small amount of cold water and dried in vacuo to give 17.50 g (65% based on TFA salt of (6R-trans)-3-[[[3,4-bis-(acetyloxy)-benzoyl]oxy]methyl]-7-amino-8-oxo-5-thia-1-azabicyclo[4.2.0]oct-2-ene-2-carboxylic acid) of the named compound.

Preparation of (6R-trans)-3-[[[(3,4-bis(acetyloxv)benzoyl]oxy]methyl]-7-[[1,1-dimethylethoxy)carbonyl]amino]-8-oxo-5-thia-1-azabicyclo[4.2.0]-oct-2-ene-2-carboxylic acid A solution of 3,4-diacetoxybenzoic acid (238.2 mg, 1 mmol) in methylene chloride (7 mL) was cooled (−26 to −32C.) under argon and cyclohexylchloroformate (152 ul, 1.05 mmol) was added followed by triethylamine (153 ul, 1.10 mmol). (6R, 7R)-7-[[1,1-dimethylethoxycarbonyl]amino]-3-(hydroxymethyl)-8-oxo-5-thia-1-azabicyclo (4.2.0) oct-2-ene-2-carboxylic acid (330.3 mg, 1.00 mmol) was immediately added then more triethylamine (153 ul, 1.10 mmol) and finally dimethylamino pyridine (32.5 mg, 0.27 mmol). The reaction was stirred for 4 hrs. It was then added to ethyl acetate (75 mL) and 1N HCl (75 mL). The ethyl acetate was then treated with a mixture of 2% sodium bicarbonate (60 mL), brine (50 mL), and n-hexanes (5 mL). The organic layer was stripped to a residue and then it was redissolved in ethyl acetate. The named compound was obtained by purification on a silica gel column by eluting with ethyl acetate, methylene chloride/methanol (9/1, v/v) and then (8/2, v/v).

Preparation of
(6R,7R)-7-[[1,1-dimethylethoxycarbonyl]amino]-3-(hydroxymethyl)-8-oxo-5-thia-1-azabicyclo(4.2.0)-oct-2-ene-2-carboxylic acid The named compound can be made as follows:
960 ml (1.92 mole) 2N NaOH are cooled to −5° C. and 216 g (0.8 mole) 7-aminocephalosporanic acid (7-ACA) are added at once with vigorous stirring. The temperature is maintained between −5° C. and 5° C. by means of a dry ice-acetone cooling bath. The hydrolysis is monitored by reversed-phase TLC or HPLC. After 15 min. at −5° C. no 7-ACA is left. The pH is immediately adjusted to 9.5 by addition of 6N HCl and the mixture is diluted with 3.0 l of dioxane. A solution of 350 g (1.6 mole) di-tert-butyl-dicarbonate in 1.0 l dioxane is added during 5 min. The pH drops to 8.0. The mixture is stirred for 60 h. The pH is kept at 8.5 by addition of conc. NaOH. The mixture is poured into 3.0 l of ethyl acetate. The water phase is separated and the organic phase is washed twice with 0.5 l water. The combined water-phases are rewashed twice with ethyl acetate. 3.0 l ethyl acetate are added and the pH is brought to 2.5 by addition of 6N HCl. At pH 3.5 a voluminous precipitate is formed which is removed by filtration on dicalite. The phases are separated. The water phase is twice extracted with ethyl acetate and the organic phases are washed with water and brine and dried with magnesium sulfate. The named produced crystallizes during evaporation of the ethyl acetate and is collected by filtration. The crystals are washed with ether and dried under vacuum. The yield is 120.0 g white crystals (45% the) m.p.: 180° C. (decomp.)

What is claimed is:

1. A process for syntheisizing an antibacterial cephalosporin compound of formula

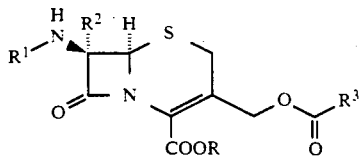

wherein R is hydrogen or a carboxylic acid protecting group; $R^1$ is hydrogen or an acyl group; $R^2$ is hydrogen or lower alkoxy; and $R^3$ is carbocyclic aryl substituted on the ring with one or more members selected from the group consisting of hydroxy, lower alkyl, amino, cyano, lower alkoxy, halogen and alkylcarboxy,
as well as the corresponding readily hydrolyzable esters, pharmaceutically acceptable salts and hydrates of these compounds where R is hydrogen, said process comprising the steps of:

a) treating a 3-hydroxymethyl $\Delta^3$-cephalosporin compound, having a carboxylic acid moiety in the 2-position, with an organic base selected from the group consisting of a tertiary amine and a quaternary ammonium hydroxide to form an organic salt therewith;

b) acylating the 3-hydroxymethyl substituent of the organic salt of the cephalosporin compound which is produced in step a) with an acylating agent which is selected to provide the desired 3-acyloxymethyl substituent on the cephalosporing compound, said reaction being carried out in a non-aqueous organic solvent; and c) converting the compound formed in step b) to the compound of formula I.

2. The process of claim 1, wherein the 3-hydroxymethyl $\Delta^3$-cephalosporin compound having a 2-carboxylic acid moiety is a compound of formula

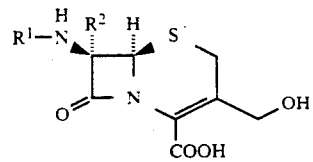

and wherein the groups $R^1$ and/or $R^2$, if susceptible to acylation conditions, are protected using suitable protecting groups before performing step (b).

3. The process of claim 1, wherein the tertiary amine has the formula:

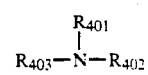

wherein $R_{400}$, $R_{401}$ and $R_{402}$ are the same or different and are $C_1$-$C_4$ lower alkyl.

4. The process of claim 3, wherein the tertiary amine is triethylamine.

5. The process of claim 1, wherein the quaternary ammonium hydroxide has the formula:

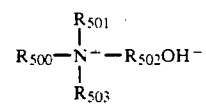

wherein $R_{500}$, $R_{501}$, $R_{502}$ and $R_{503}$ are the same or different and are $C_1$-$C_4$ lower alkyl.

6. The process of claim 1, wherein the acylating agent is an acid halide.

7. The process of claim 6, wherein the acid halide is an acid fluoride.

8. The process of claim 1, wherein the non-aqueous organic solvent is selected from the group consisting of methylene chloride, 1,2 dichloroethane, acetonitrile and tetrahydrofuran.

9. The process of claim 8, wherein the non-aqueous organic solvent is methylene chloride.

10. The process of claim 9, wherein the compound of formula I is [6R-[6alpha,7beta(Z)]]-7-[[[(2-amino[2-amino-2-oxo-ethoxy)-imino]-4-thiazolyl]acetyl-]amino]-3-[[(3,4-dihydroxybenzoyl)oxy]-methyl]-8-oxo-5-thia-1-azabicYclo-[4.2.0]oct-2-ene-2-carboxylic acid.

11. A process for synthesizing [6R-[6alpha,7beta(Z)]]-7-[[[(2-amino[2-amino-2-oxo-ethoxy)imino]-4-thiazolyl]acetyl]amino]-3-[[(3,4-dihydroxybenzoyl)oxy]methyl]-8-oxo-5-thia-1-azabicyclo-[4.2.0]oct-2-ene-2-carboxylica cid, said process comprising the steps of:

a) treating a compound of formula:

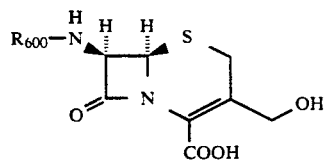

wherein $R_{600}$ is an amino protecting group, with an organic base selected from the group consisting of a tertiary amine and a quaternary ammonium hydroxide to form an organic salt with the carboxylic acid moiety in the 2-position;

b) acylating the compound which is produced in step a) with 3,4-diacetoxybenzoyl fluoride in a non-aqueous organic solvent;

c) removing the organic base from the compound produced in d) reacting the compound obtained in step c) after removal of protecting group $R_{600}$ with S-2-mercaptobenzthiazoyl-2-(2-aminothiazol-4-yl)-2-(Z)-formamidoethoxyiminoacetate to obtain [6R-[6alpha,7beta (Z)]]-70[[[(2-amino[2-amino-2-oxo ethoxy)imino]-4-thiazolyl]acetyl]amino]-3-[[(3,4-dihydroxybenzoyl)oxy]methyl]-8-oxo-5-thia-1-azabicyclo-[4.2.0]oct-2-ene-2-carboxylic acid.

12. The process of claim 11, wherein the tertiary amine has the formula

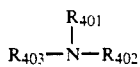

wherein $R_{400}$, $R_{401}$ and $R_{402}$ are the same or different and are $C_1$–$C_3$ lower alkyl.

13. The process of claim 12, wherein the tertiary amine is triethylamine.

14. The process of claim 11, wherein the quaternary ammonium hydroxide has the formula

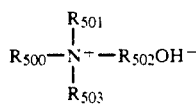

wherein $R_{500}$, $R_{501}$, $R_{502}$ and $R_{503}$ are the same or different and are $C_1$–$C_4$ lower alkyl.

15. The process of claim 11, wherein the non-aqueous organic solvent is selected from the group consisting of methylene chloride, 1,2-dichloroethane, acetonitrile and tetrahydrofuran.

16. The process of claim 15, wherein the non-aqueous organic solvent is methylene chloride.

17. The process of claim 11, wherein $R_{600}$ is 1,1-dimethyl(ethoxy)carbonyl.

18. A process for synthesizing an antibacterial $\Delta^3$-cephaslosporin compound of formula

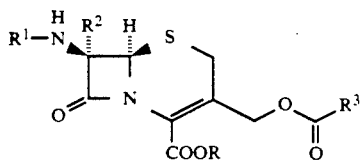

wherein R is hydrogen or a carboxylic acid protecting group; $R^1$ is hydrogen or an acyl group; $R^2$ is hydrogen or lower alkoxy; and $R^3$ is carbocyclic aryl substituted on the ring with one or more members selected from the group consisting of hydroxy, lower alkyl, amino, cyano, lower alkoxy, halogen and alkylcarboxy, as well as the corresponding readily hydrolyzable esters, pharmaceutically acceptable salts and hydrates of these compounds where R is hydrogen, said process comprising acylating the salt of a 2-carboxylic acid 3-hydroxymethyl $\Delta^3$-cephalosporin compound and an organic base selected from the group consisting of tertiary amine and quaternary ammonium hydroxide with an acylating agent which is selected to provide the desired 3-acyloxymethyl substituent in the compound of formula I, said reaction being carried out in a non-aqueous organic solvent.

19. The process of claim 18, wherein the tertiary amine has the formula:

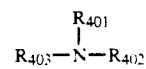

wherein $R_{400}$, $R_{401}$ and $R_{402}$ are the same or different and are $C_1$–$C_4$ lower alkyl.

20. The process of claim 19, wherein the organic base is triethylamine.

21. The process of claim 18, wherein the quaternary ammonium hydroxide has the formula:

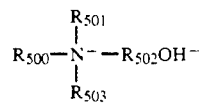

wherein $R_{500}$, $R_{501}$, $R_{502}$ and $R_{503}$ are the same or different and are $C_1$–$C_4$ lower alkyl.

22. The process of claim 18, wherein the acylating agent is an acid halide.

23. The process of claim 22, wherein the acid halide is an acid fluoride.

24. The process of claim 18, wherein the non-aqueous organic solvent is selected from the grouP consisting of methylene chloride, 1,2 dichloroethane, acetonitrile and tetrahydrofuran.

25. The process of claim 24, wherein the non-aqueous organic solvent is methylene chloride.

26. The process of claim 18, wherein the compound of formula I is [6R-[6alpha,7beta(Z)]]-7-[[[(2-amino[2-amino-2-oxo-ethoxy)-imino]-4-thiazolyl-]acetyl]amino]-3-[[(3,4dihydroxybenzoyl)oxy]-methyl]-8-oxo-5-thia-1-azabicyclo[4.2.0]oct-2-ene-2-carboxylic acid.

27. The process of claim 26, wherein the organic base is triethylamine.

28. The process of claim 26, wherein the non-aqueous organic solvent is methylene chloride.

* * * * *

UNITED STATES PATENT AND TRADEMARK OFFICE
CERTIFICATE OF CORRECTION

PATENT NO. : 5,112,967

DATED : May 12, 1992

INVENTOR(S) : Dennis Dalton Keith, Chung-Chen Wei and Kevin Francis West

It is certified that error appears in the above-identified patent and that said Letters Patent is hereby corrected as shown below:

In claim 1, column 21, delete the chemical structure between lines 37-45 and insert therefor —

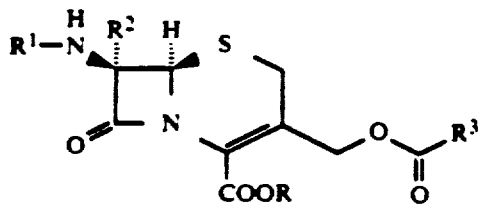

—.

In claim 1, column 21, line 66, delete "cephalosporing" and insert therefor — cephalosporin —.

In claim 3, column 22, delete the chemical structure between lines 20-23 and insert therefor —

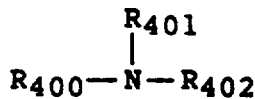

—.

In claim 3, column 22, line 25, delete "$C_1$-$C_4$" and insert therefor — $C_1$-$C_3$ —.

UNITED STATES PATENT AND TRADEMARK OFFICE
CERTIFICATE OF CORRECTION

PATENT NO. : 5,112,967
DATED : May 12, 1992
INVENTOR(S) : Dennis Dalton Keith, Chung-Chen Wei and Kevin Francis West It is certified that error appears in the above-identified patent and that said Letters Patent is hereby corrected as shown below:

Column 22, claim 10, line 52, delete "azabic Y clo" and insert therefor -- azabicyclo --.

Col. 22, lines 53-54, line 53, delete "[6R-[6alpha,7beta(Z)]" and insert therefor --[6R-[6alpha,7beta(Z)]] --.

Col. 22, line 57, delete "carboxylica cid" and insert therefor -- carboxylic acid --.

In claim 11, column 23, line 10, after "produced in" add -- step b); and --.

In claim 11, column 23, line 16, delete "-70[[[" and insert therefor -- -7-[[[ --.

In claim 11, column 23, line 16, between "oxo ethox-" add -- - --.

In claim 12, column 23, delete the chemical structure between lines 22-26 and insert therefor --

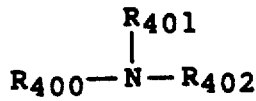

--.

UNITED STATES PATENT AND TRADEMARK OFFICE
CERTIFICATE OF CORRECTION

PATENT NO. : 5,112,967
DATED : May 12, 1992
INVENTOR(S) : Dennis Dalton Keith, Chung-Chen Wei and Kevin Francis West It is certified that error appears in the above-identified patent and that said Letters Patent is hereby corrected as shown below:

In claim 19, column 24, delete the chemical structure between lines 20-23 and insert therefor --

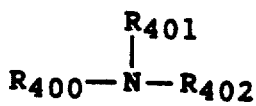

--.

In claim 19, column 24, line 26, delete "$C_1-C_4$" and insert therefor -- $C_1-C_3$ --.

In claim 24, column 24, line 44, change "grouP" to -- group --.

In claim 26, column 24, line 52, between 3,4 and dihydroxybenzoyl) insert -- - --.

Signed and Sealed this

Fourteenth Day of September, 1993

Attest:

Attesting Officer

BRUCE LEHMAN
Commissioner of Patents and Trademarks